US010072406B2

(12) United States Patent
Hall et al.

(10) Patent No.: US 10,072,406 B2
(45) Date of Patent: Sep. 11, 2018

(54) QUIET TOILET APPARATUS

(71) Applicants: David R. Hall, Provo, UT (US); Dan Allen, Springville, UT (US); Ben Swenson, Lehi, UT (US); Joshua Larsen, Spanish Fork, UT (US); Jared Reynolds, Pleasant Grove, UT (US)

(72) Inventors: David R. Hall, Provo, UT (US); Dan Allen, Springville, UT (US); Ben Swenson, Lehi, UT (US); Joshua Larsen, Spanish Fork, UT (US); Jared Reynolds, Pleasant Grove, UT (US)

(*) Notice: Subject to any disclaimer, the term of this patent is extended or adjusted under 35 U.S.C. 154(b) by 37 days.

(21) Appl. No.: 15/176,453

(22) Filed: Jun. 8, 2016

(65) Prior Publication Data

US 2017/0356176 A1 Dec. 14, 2017

(51) Int. Cl.

| | |
|---|---|
| ***A61F 11/06*** | (2006.01) |
| ***E03D 9/00*** | (2006.01) |
| ***E03D 11/02*** | (2006.01) |
| ***A47K 13/30*** | (2006.01) |
| ***G10K 11/178*** | (2006.01) |

(52) U.S. Cl.

CPC ................ *E03D 9/00* (2013.01); *A47K 13/30* (2013.01); *E03D 11/02* (2013.01); *G10K 11/178* (2013.01); *E03D 2201/20* (2013.01); *G10K 2210/105* (2013.01); *G10K 2210/3046* (2013.01); *G10K 2210/30231* (2013.01)

(58) Field of Classification Search

CPC .................................................. E03D 2201/20

See application file for complete search history.

(56) References Cited

U.S. PATENT DOCUMENTS

| | | | | |
|---|---|---|---|---|
| 4,160,295 A * | 7/1979 | Putyra | A47K 13/24 4/420 |
| 7,194,776 B1 * | 3/2007 | Lastuka | E03D 13/00 340/603 |
| 9,743,903 B1 * | 8/2017 | Hall | A61B 7/008 |
| 2006/0039569 A1 * | 2/2006 | Antaki | G10K 11/1788 381/71.1 |
| 2008/0082022 A1 * | 4/2008 | Brohan | A61B 5/208 600/573 |
| 2015/0287400 A1 * | 10/2015 | Christoph | H04S 7/301 381/71.11 |
| 2016/0071508 A1 * | 3/2016 | Wurm | G10K 11/1784 381/58 |
| 2016/0118036 A1 * | 4/2016 | Cheatham, III | G10K 11/178 380/252 |

FOREIGN PATENT DOCUMENTS

| | | | |
|---|---|---|---|
| GB | 2446474 | * | 8/2008 |
| JP | 5-132986 | * | 5/1993 |
| JP | 10-14823 | * | 1/1998 |

* cited by examiner

*Primary Examiner* — J. Casimer Jacyna

(57) ABSTRACT

A quiet toilet apparatus disclosed. Microphones and circuitry are used to receive and detect one or more virtual point source locations and propagation directions of unwanted toilet noise. Speakers are used to create one or more synthesized wave fronts resulting in cancelation and reduction of unwanted toilet noise. The speakers, microphones and circuitry may be located within a toilet seat of a toilet or at a remote location. A user device or remote device may be connected to the noise reduction toilet apparatus for data recording, collection, reporting, and electronic noise filtering.

2 Claims, 10 Drawing Sheets

QUIET TOILET APPARATUS

BACKGROUND

Field of the Invention

This invention relates to methods and systems for reducing unwanted toilet noise.

Background of the Invention

Attempts have been made to mask unwanted toilet noise using music and white noise. Both of these methods create additional noise and do not reduce the overall noise generated by using a toilet.

Antaki, in US 2006/0039569, teaches a noise canceling toilet which uses one or more speakers positioned within a distance of less than two wavelengths or 4.5 inches from a source of the noise [72]. The way Antaki cancels noise is problematic because an inner toilet bowl dimension can be longer than 12 inches from front to back and longer than 7 inches from side to side and more than 6 inches in depth from the toilet seat to a reflective surface in the toilet making noise cancelation impossible in some cases and ineffective in other cases.

SUMMARY

In response to the continuing need for a noise canceling toilet, a quiet toilet apparatus which includes one or more microphones for detecting toilet noise, circuitry, and data processing for determining a virtual point source noise location and wave propagation direction for the purpose of generating a synthesized wave front using one or more speakers is disclosed.

A quiet toilet apparatus for providing noise canceling is disclosed. Microphones and circuitry are used to receive unwanted toilet noise and determine one or more virtual point source noise locations and wave propagation directions therefrom. An array of speakers may be used to create one or more synthesized wave fronts resulting in cancelation and reduction of unwanted toilet noise. The synthesized wave fronts may be transmitted towards a virtual point source location or away from a virtual point source location. Because a synthesized wave front is created based on a virtual noise point source position and direction, the synthesized sound need not be transmitted within a close proximity to the noise source as is taught in the prior art. The speakers, microphones and circuitry may be located within a toilet seat of a toilet. One or more synthesized wave fronts may be transmitted above and/or below a toilet seat to achieve effective noise cancelation. One or more synthesized wave fronts may be transmitted from a location remote from a toilet and still achieve effective noise cancelation.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, may be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
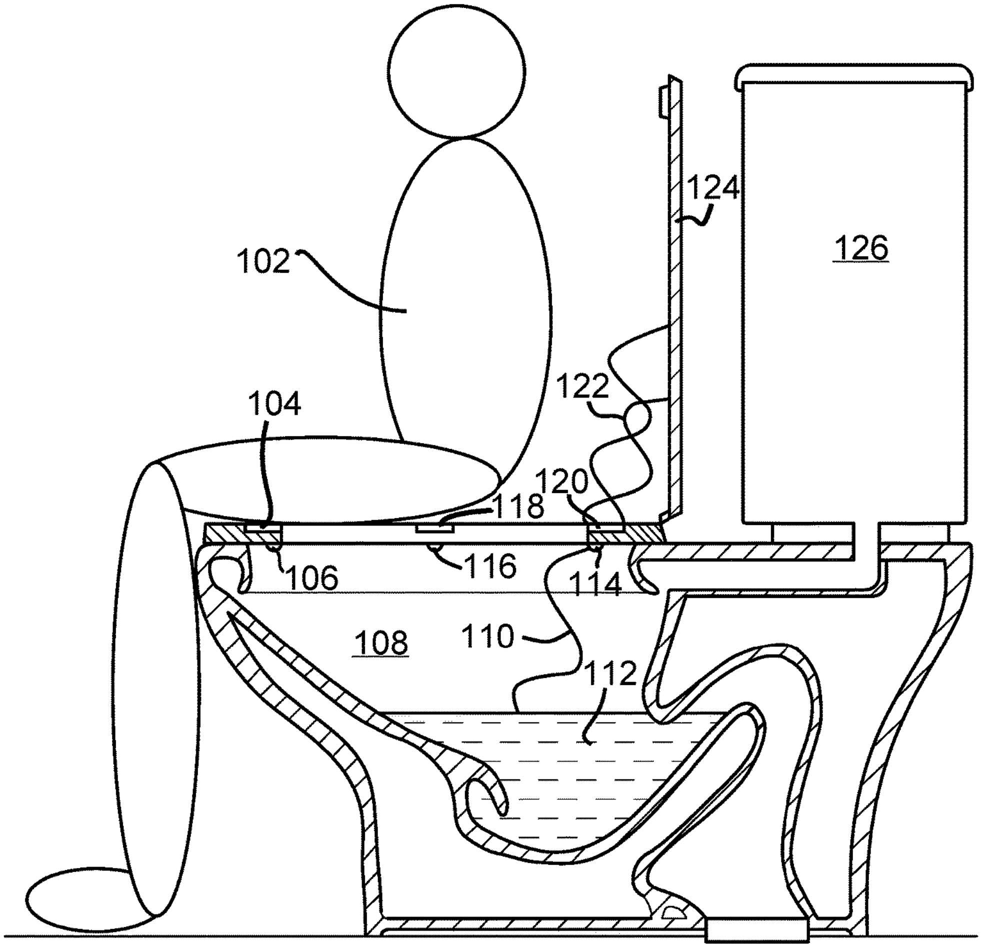
FIG. 1 is a side view of a toilet in accordance with an embodiment of the invention.

FIG. 1 shows a cross-sectional view of a user 102 sitting on a toilet. Unwanted noise or unwanted sound waves 110 which radiate from an inside bowl area 108 are received by one or more microphones 106 and 114. Microphones 106 and 114 may be a single microphone or may comprise an array of microphones pointed in different directions. An array of microphones (shown in FIG. 4 at 404) may be configured in a hemispherical or spherical shape allowing a direction and intensity of noise to be determined. An array of microphones may be used to determine a direction and position of a virtual point source of unwanted noise or sound located within a bowl of a toilet. Circuitry connected to microphones 106 and 114 may invert the unwanted noise or unwanted sound waves 110 and output an inverted unwanted sound wave signals to one or more speakers 116, 118, 104, and 120 which transmit the inverted unwanted noise or unwanted sound waves. The speakers 116, 118, 104 and 120 may each comprise an array of speakers pointed in different directions. The array of speakers (shown in FIG. 4 at 406) may synthesis a wave field of inverted unwanted toilet noise based on a predetermined virtual point source location and direction. The inverted unwanted sound waves or wave field may mix or combine with the unwanted sound waves to cancel or substantially cancel each other. The speakers may transmit the inverted synthesized wave field signal in a similar direction compared to a propagation direction of received unwanted sound waves. The speakers may transmit the inverted signal in a downward direction into the toilet bowl, in an upward direction out of the toilet bowl, or in a combination of directions based on a direction of the unwanted sound wave fields detected by one or more microphones. Additional microphones may be located on a toilet lid 124, on toilet tank 126, or at a remote location such as a bathroom door. The additional microphones may provide feedback about noise cancelation in order to calibrate the output of one or more speakers and the wave fields generated by the wave fields. Additional speakers may also be located on lid 124, on toilet tank 126, or at a remote location such as a bathroom door and may provide additional noise cancelation radiation. Microphones 106 and 114 may be located on or in a toilet seat as shown in FIG. 1. Microphones 106 and 114 may transmit in multiple directions including into the bowl and toward a user or a lid of the toilet. Lid 124, the toilet seat, or an inside of the toilet may be made of sound absorptive material such as mass loaded vinyl, high density material, anechoic material, or geometric sound canceling formations. Unwanted sound 110 is radiated from a bowl area 108 and received by microphone 114. Microphone 114 provides an unwanted sound wave signal to circuitry (not shown). The circuitry determines one or more virtual point source locations of the unwanted sound wave signals provided by an array of microphones. The circuitry then outputs a synthesized inverted unwanted sound wave field signal to one or more speakers to create a synthesized wave front 122. The speakers may be chosen based on a virtual point location and a direction of propagation of the unwanted sound. A virtual point source location may be determined based on an array of microphones which may be located at microphone 114. The virtual point source location may be located in three dimensional space within a bowl of a toilet and along a propagation axis of unwanted wave 110. The microphone array 114 may be formed in a hemispherical or spherical shape and the direction of propagation may be determined, in part, based on an intensity received at one or more microphones in the array. Speaker 120 may also comprise an array of speakers forming a hemispherical or spherical shape and one or more of the speakers 120 may be used to create and transmit a synthesized wave front of the inverted unwanted sound wave signal 122 is a similar direction compared to the propagation direction of the unwanted sound wave 110. If microphone array 114 receives multiple unwanted sound waves which have different propagation directions, then multiple virtual signal point sources may be determined and multiple synthesized wave fronts may be sent by multiple speakers within an array of speakers in different propagation directions.

Figure 2A:
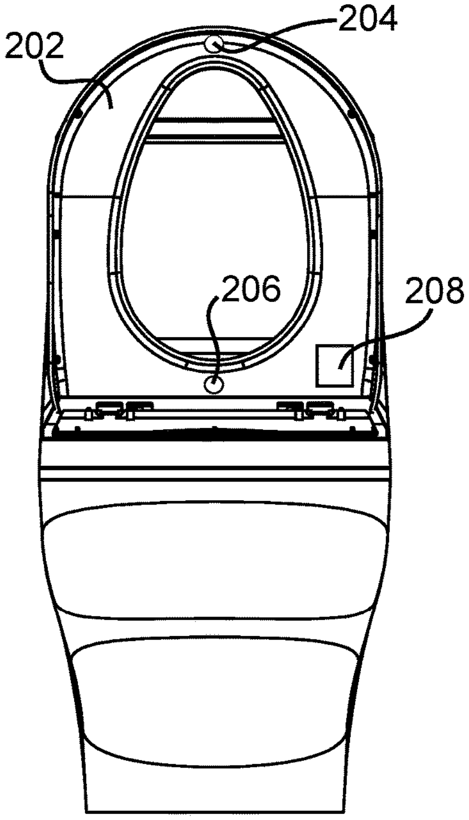
FIG. 2*a* is a bottom view of a toilet seat in accordance with an embodiment of the invention.
Figure 2B:
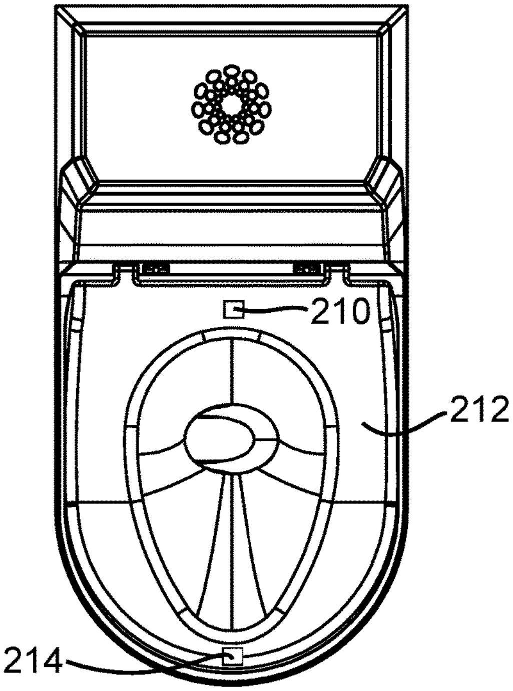
FIG. 2*b* is a top view of a toilet seat in accordance with an embodiment of the invention.

FIGS. 2*a* and 2*b* show a bottom side 202 of a toilet seat and a top side of a toilet seat 212. Shown at 204 and 206 are combination microphone speaker arrays which may be used to transmit inverted sound waves and receive unwanted sound waves. The speakers may transmit inverted sound waves in a downward direction toward a sound point origin location, virtual sound point, or sound point reflection location within the toilet bowl. The transmitted inverted sound waves may be transmitted in a propagation direction similar to a reflected unwanted sound reflection path or along a similar propagation directional axis. One or more microphones within the arrays 206 and 204 may provide directional information about a propagation path of an unwanted sound wave. The microphones may receive different amplitude signals resulting from reception of unwanted sound waves. The different amplitude signals may be used to determine a virtual point location and propagation direction of the unwanted sound waves. Circuitry 208 may receive one or more microphone input signals with unwanted sound wave frequency and direction information. The circuitry may then invert the received signal and transmit the inverted unwanted sound wave signal to one or more speakers in an array of speakers within 204 or 206. The circuitry may be powered by a battery, by a power supply with the toilet, or by a non-contact inductive power source within the toilet seat and another fixed part or the toilet such as the toilet tank, or toilet bowl. The speakers and microphones may be placed adjacent to each other in arrays or be separate arrays which may be spherical or hemispherical arrays of speakers and/or microphones.

Shown at 210 and 214 may be combination microphone speaker arrays which may be used to transmit inverted sound waves and receive unwanted sound waves. The speakers may transmit inverted sound waves in an upward direction toward a sound point origin location or reflection location outside of the toilet bowl. The transmitted inverted sound waves may be transmitted in a propagation direction similar to a reflected unwanted sound reflection path or along a similar propagation directional axis. One or more microphones within the arrays 210 and 214 may provide directional information about a propagation path of an unwanted sound wave. The microphones may receive different amplitude signals resulting from reception of unwanted sound waves. The different amplitude signals may be used to determine a propagation direction of the unwanted sound waves. Circuitry 208 of FIG. 2*a* may receive one or more microphone input signals with unwanted sound wave frequency and direction information. The circuitry may then invert the received signal and transmit the inverted unwanted sound wave signal to one or more speakers in an array of speakers within 210 or 214. The circuitry may be powered by a battery, by a power supply with the toilet, or by a non-contact inductive power source within the toilet seat and another fixed part or the toilet such as the toilet tank, or toilet bowl. The speakers and microphones may be placed adjacent to each other in arrays or be separate arrays which may be spherical or hemispherical arrays of speakers and/or microphones.

Figure 3:
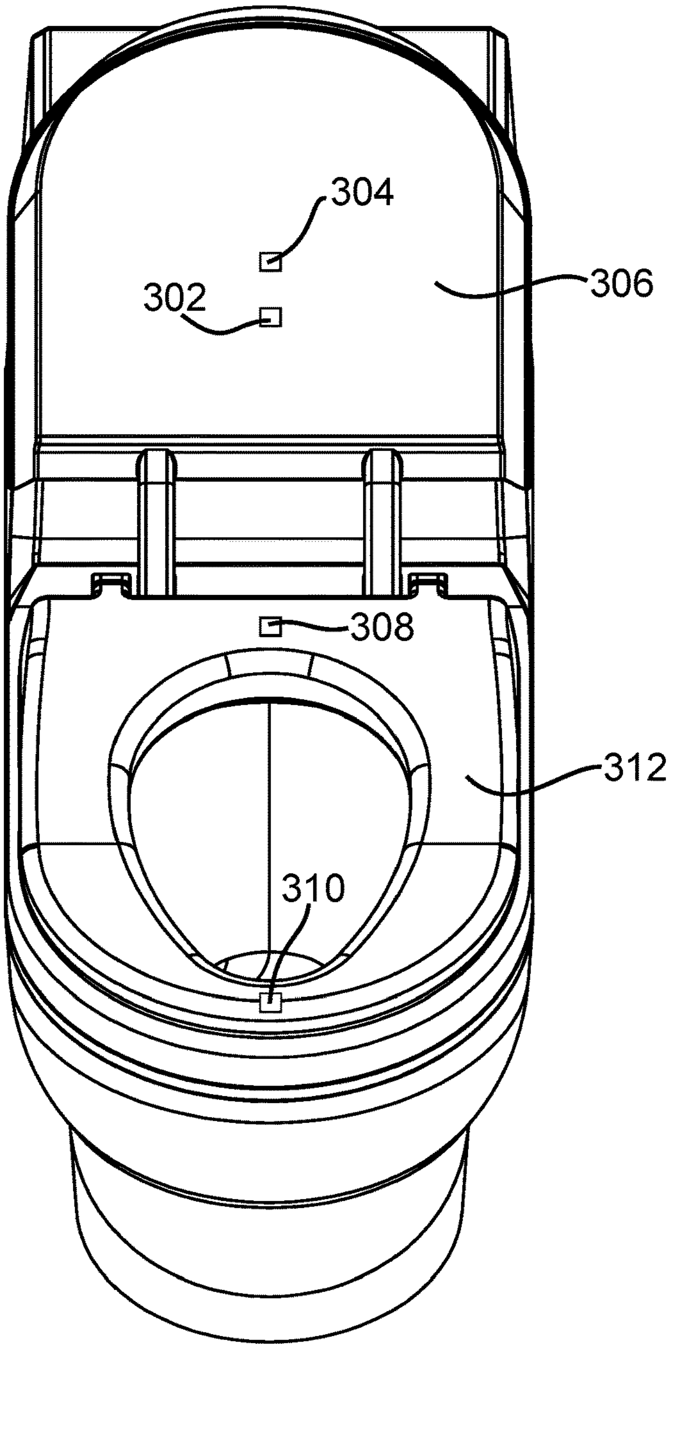
FIG. 3 is a perspective view of a toilet seat in accordance with an embodiment of the invention.

Referring now to FIG. 3, combination microphone speaker arrays 302, 304, 306 and 308 may be used to transmit inverted sound waves and receive unwanted sound waves. The speakers may transmit inverted sound waves in an upward direction toward a sound point origin location or reflection location outside of the toilet bowl. The transmitted inverted sound waves may be transmitted in a propagation direction similar to a reflected unwanted sound reflection path or along a similar propagation directional axis. One or more microphones within the arrays 302, 304, 306 and 308 may provide directional information about a propagation path of an unwanted sound wave. The microphones may receive different amplitude signals resulting from reception of unwanted sound waves. The different amplitude signals may be used to determine a propagation direction of the unwanted sound waves. If a microphone array receives multiple unwanted sound waves which have different propagation directions, then multiple virtual signal point sources may be determined and multiple synthesized wave fronts may be sent by multiple speakers within an array of speakers in different propagation directions. Circuitry 208 of FIG. 2*a* may receive one or more microphone input signals with unwanted sound wave frequency and direction information. The circuitry may include a processor for performing digital signal processing of microphone inputs and speaker outputs. The processor may also have memory and programming which allows a virtual noise point source location to be determined based on one or more microphone inputs. The processor may also include programming which allow a wave front to be synthesized using one or more speaker outputs. The circuitry may invert the received signal or wave front and transmit the inverted unwanted sound wave signal or synthesized wave front signal to one or more speakers in an array of speakers within 302, 304, 306 and/or 308. The circuitry may be powered by a battery, by a power supply with the toilet, or by a non-contact inductive power source within the toilet seat and another fixed part or the toilet such as the toilet tank, or toilet bowl. The speakers and microphones may be placed adjacent to each other in arrays or be separate arrays which may be spherical or hemispherical arrays of speakers and/or microphones. The microphones and/or speakers 302, 304 may be positioned on a lid 306 of a toilet seat 312 as shown in FIG. 3 and provide feedback to one or more circuits associated with microphone and/or speakers.

Figure 4:
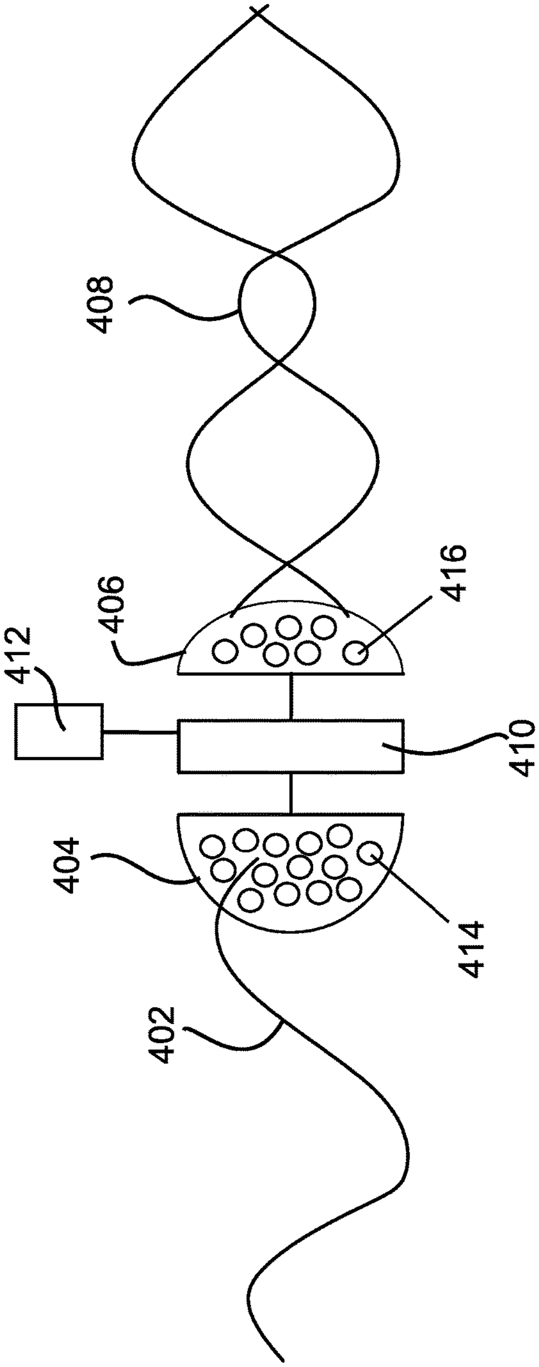
FIG. 4 is a diagram of unwanted sound and inverted unwanted sound in accordance with an embodiment of the invention.

FIG. 4 shows unwanted sound waves 402 entering microphone array 404. The unwanted sound waves 402 create a wave field which imparts direction and location information into individual microphones 414 of the microphone array 404. A sound intensity and direction received at one or more microphones of the array 404 may be correlated with a physical microphone location on a microphone array 404. The intensity and direction information may be used to determine a point source of noise and a direction of noise propagation from the noise source. Microphone array 404 may comprise a plurality of microphones positioned in a spherical or hemispherical shape. Microphone array 404 provides an unwanted sound wave input signals to circuit 410. Circuit 410 may contain active and passive circuitry which inverts the unwanted sound wave signal and outputs the inverted signal to speaker 406. Circuit 410 may be connected to a processor 412. Processor 412 may be powered by a battery or a power supply. Processor 412 may perform digital signal processing in order to determine a virtual point source location and direction of noise propagation from the virtual point source. Processor 412 may also output one or more digital signal allowing a synthesized wave front to be created by one or more speakers 416 of speaker array 406. Speaker array 406 may have multiple speakers formed in a hemispherical or spherical shape allowing for a synthesized wave front to be created therefrom. Speaker array 406 may transmit an inverted wave front signal as an inverted sound wave signal 408 in a similar direction or to a similar location compared to the direction or location of unwanted sound waves 402. As waves 402 and 408 mix the result is cancelation of unwanted sound or substantial reduction of unwanted sound.

Figure 5:
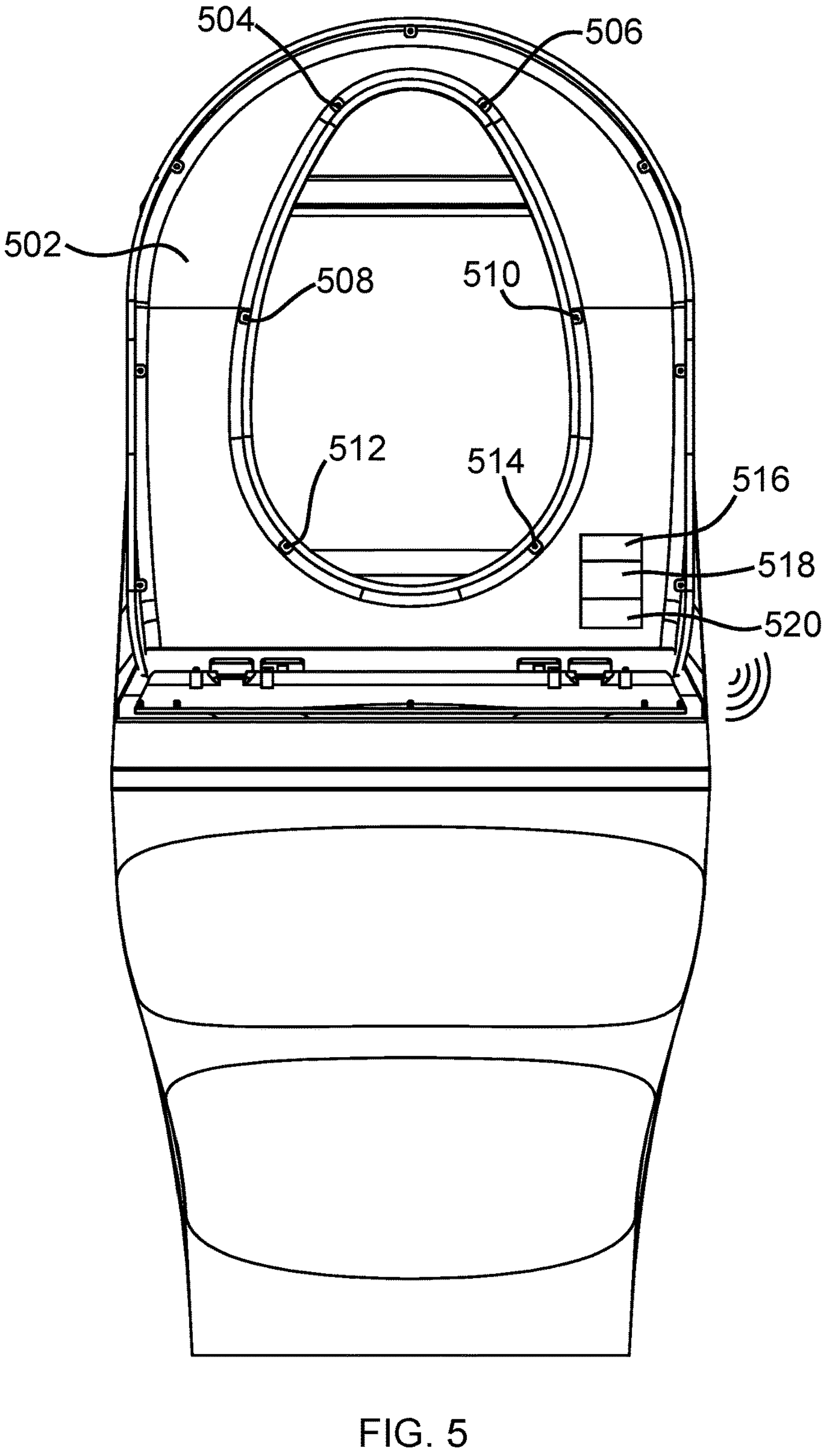
FIG. 5 is a bottom view of a toilet seat in accordance with an embodiment of the invention.

Referring now to FIG. 5, combination microphone speaker arrays 504, 506, 508, 510, 512 and 514 may be used to transmit inverted sound waves and receive unwanted sound waves. The speakers may transmit inverted sound waves in a downward direction toward a sound point origin location or reflection location inside of the toilet bowl or to a virtual space. The transmitted inverted sound waves may be transmitted in a propagation direction similar to a reflected unwanted sound reflection path or along a similar propagation directional axis. One or more microphones within the arrays 504, 506, 508, 510, 512 and 514 may provide directional information about a propagation path of an unwanted sound wave. The microphones may receive different amplitude signals resulting from reception of unwanted sound waves. The different amplitude signals may be used to determine a propagation direction of the unwanted sound waves. Circuitry 518 may receive one or more microphone input signals with unwanted sound wave frequency and direction information. The circuitry may then invert the received signal and transmit the inverted unwanted sound wave signal to one or more speakers in an array of speakers within 504, 506, 508, 510, 512 and/or 514. The circuitry may be powered by a power source 516 the circuitry 518 may include a processor for performing digital signal processing. The power source may be a battery, a power supply within the toilet, or a non-contact inductive power source within multiple parts of the toilet such as the toilet seat and another location of the toilet. A communication section 520 may wirelessly transmit information gathered by the microphones to a remote computer or user device. The information transmitted may include noises from within the toilet including bowel movements, bowel movement frequency, urination duration, urination frequency, user speech, user commands, flatulence, etc. The information may be used to provide medical data to doctors, tracking of digestive health, tracking of urinary system health, voice recognition commands, talking on a telephone while in a restroom. Sounds picked up by the microphones may be used to cancel unwanted sounds such as urination sounds and amplify wanted sounds such as a user's voice talking to a friend over the Internet through microphones in the toilet. The canceled sounds may be canceled by mixing sound waves in free space or by canceling or filtering out unwanted sound signals in electronic communications. The speakers and microphones may be placed adjacent to each other in arrays or be separate arrays which may be spherical or hemispherical arrays of speakers and/or microphones. The microphones and/or speakers 504, 506, 508, 510, 512 and 514 may be positioned on a toilet seat 502 and provide feedback to one or more circuits associated with microphone and/or speakers. The speakers may be used to transmit desired sounds in addition to inverted unwanted sound waves. For instance, if a user is talking to a friend over the Internet using the microphones and the speakers on the toilet, the microphones and speakers may also be providing noise canceling features while the user is using the toilet. A user may pair the noise canceling toilet to a user device and talk on the telephone hands free without worrying about toilet noises being transmitted through to the other end of the telephone call.

Figure 6:
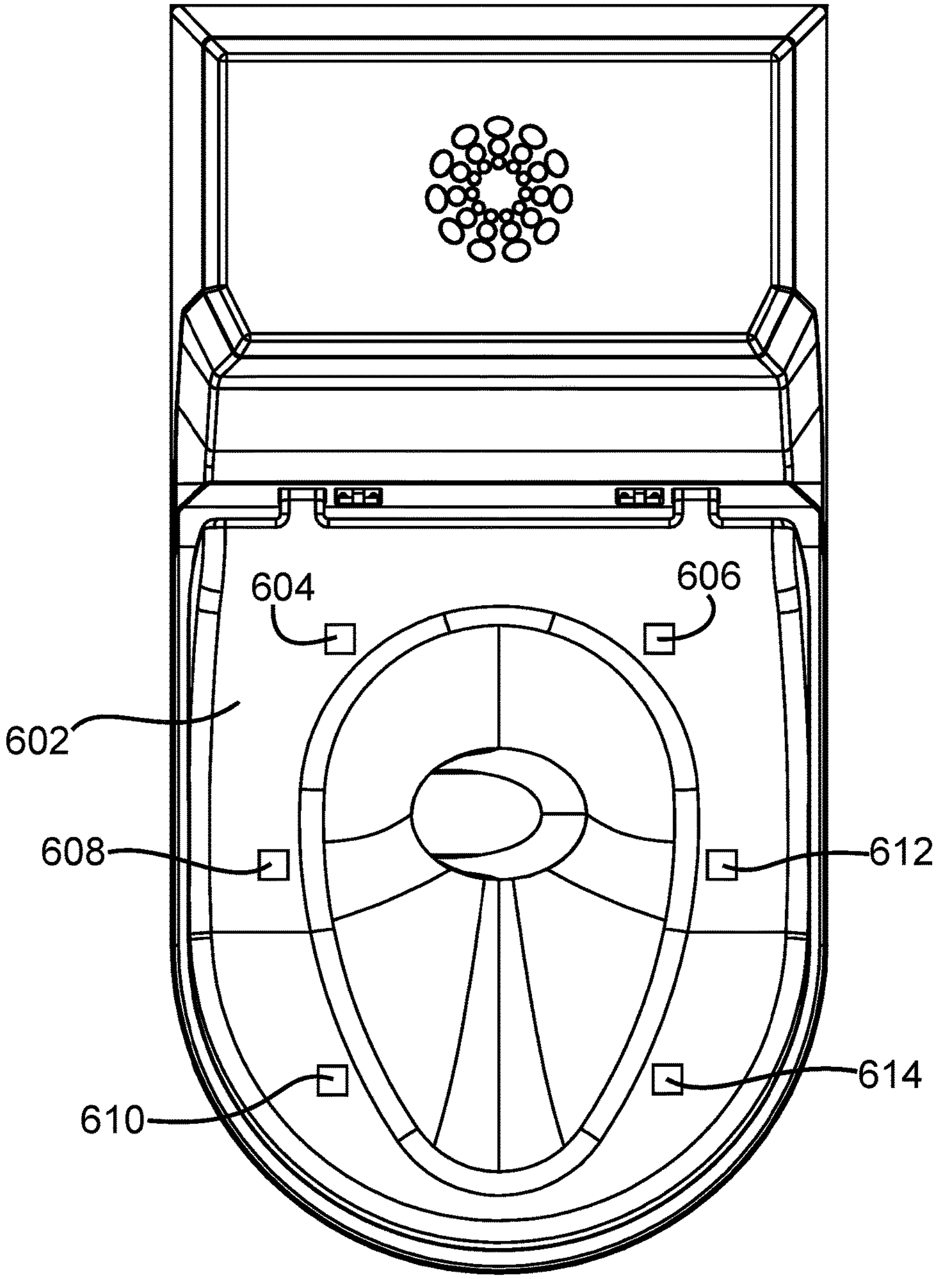
FIG. 6 is top view of a toilet seat in accordance with an embodiment of the invention.

In FIG. 6, combination microphone speaker arrays 604, 606, 608, 610, 612 and 614 may be used to transmit inverted sound waves and receive unwanted sound waves. The speakers may transmit inverted sound waves in an upward direction toward a sound point origin location or reflection location outside of the toilet bowl or to a virtual space. The transmitted inverted sound waves may be transmitted in a propagation direction similar to a reflected unwanted sound reflection path or along a similar propagation directional axis. One or more microphones within the arrays 604, 606, 608, 610, 612 and 614 may provide directional information about a propagation path of an unwanted sound wave. The microphones may receive different amplitude signals resulting from reception of unwanted sound waves. The different amplitude signals may be used to determine a propagation direction of the unwanted sound waves. Circuitry 518, of FIG. 5, may receive one or more microphone input signals with unwanted sound wave frequency and direction information. The circuitry may then invert the received signal and transmit the inverted unwanted sound wave signal to one or more speakers in an array of speakers within 604, 606, 608, 610, 612 and/or 614. The circuitry may be powered by a power source 516 of FIG. 5. The power source may be a battery, a power supply within the toilet, or a non-contact inductive power source within multiple parts of the toilet such as the toilet seat and another location of the toilet. A communication section 520, of FIG. 5, may wirelessly transmit information gathered by the microphones to a remote computer or user device. The information transmitted may include noises from within the toilet including bowel movements, bowel movement frequency, urination duration, urination frequency, user speech, user commands, flatulence, etc. The information may be used to provide medical data to doctors, tracking of digestive health, tracking of urinary system health, voice recognition commands, talking on a telephone while in a restroom. Sounds picked up by the microphones may be used to cancel unwanted sounds such as urination sounds and amplify wanted sounds such as a user's voice talking to a friend over the Internet through microphones in the toilet. The canceled sounds may be canceled by mixing sound waves in free space or by canceling or filtering out unwanted sound signals in electronic communications. The speakers and microphones may be placed adjacent to each other in arrays or be separate arrays which may be spherical or hemispherical arrays of speakers and/or microphones. The microphones and/or speakers 604, 606, 608, 610, 612 and 614 may be positioned on a toilet seat 602 and provide feedback to one or more circuits associated with microphone and/or speakers. The speakers may be used to transmit desired sounds in addition to inverted unwanted sound waves. For instance, if a user is talking to a friend over the Internet using the microphones and the speakers on the toilet, the microphones and speakers may also be providing noise canceling features while the user is using the toilet. A user may pair the noise canceling toilet to a user device and talk on the telephone hands free without worrying about toilet noises being transmitted through to the other end of the telephone call.

Figure 7:
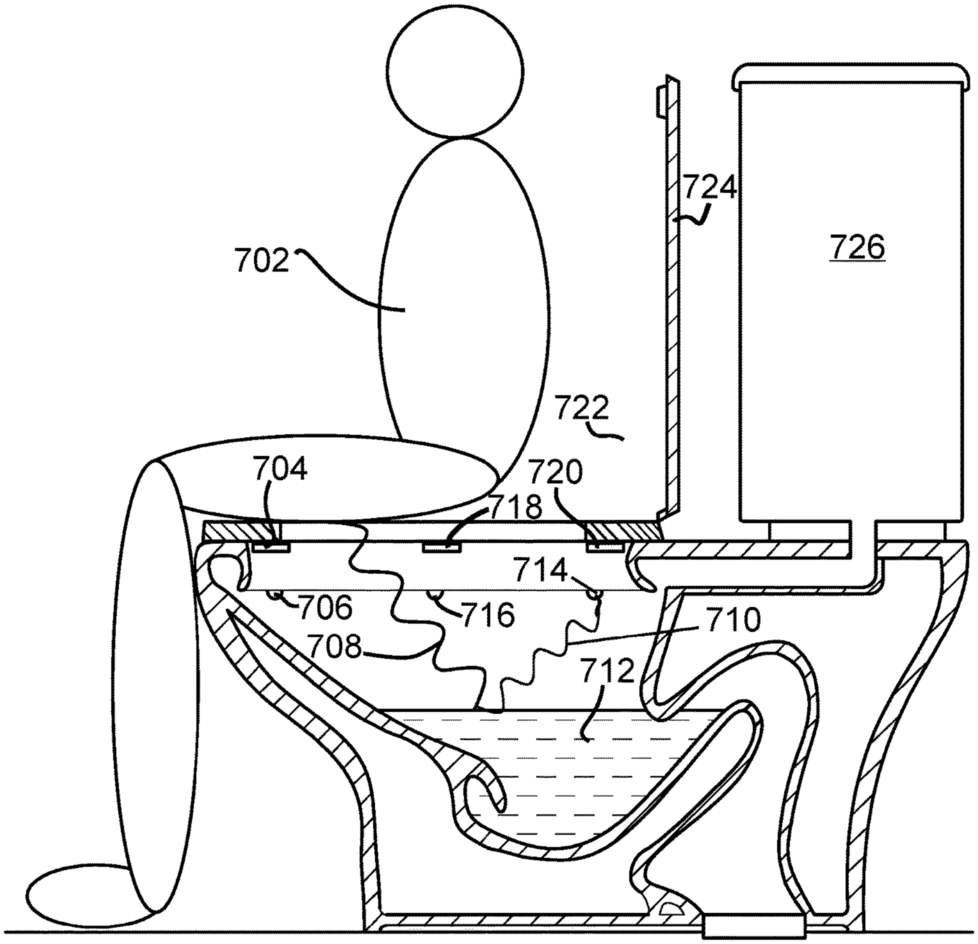
FIG. 7 is a side view of a toilet in accordance with an embodiment of the invention.

In FIG. 7, a cross-sectional view of a user 702 sitting on a toilet. Unwanted noise or unwanted sound waves 708 which radiate from inside of a bowl area of a toilet 726 are received by one or more microphones 706, 716, 714, 704, 718, and 720. Microphones 706, 716, 714, 704, 718, and 720 may each be a single microphone or may each be an array of microphones pointed in different directions. An array of microphones may be used to determine a direction and position of a virtual point source of unwanted noise or sound located within a bowl of a toilet. Circuitry connected to microphones 706, 716, 714, 704, 718, and 720 invert the unwanted noise or unwanted sound waves 708 and output an inverted unwanted sound wave signal to one or more speakers 706, 716, 714, 704, 718, and 720 which transmit the inverted unwanted noise or inverted unwanted sound waves 710. The speakers 706, 716, 714, 704, 718, and 720 may each comprise an array of speakers pointed in different directions. The array of speakers may synthesis a wave field of inverted unwanted toilet noise based on a predetermined virtual point source location and direction. The inverted unwanted sound waves or wave field may mix or combine with the unwanted sound waves to cancel or substantially cancel each other. The speakers may transmit the inverted synthesized wave field signal in a similar direction compared to a propagation direction of received unwanted sound waves. The speakers may transmit the inverted signal in a downward direction into the toilet bowl, in an upward direction out of the toilet bowl, or in a combination of directions based on a direction of the unwanted sound wave fields detected by one or more microphones. The inverted unwanted sound waves 710 mix or combine with unwanted sound waves to cancel or substantially cancel each other. The speakers may transmit the inverted signal in a similar direction compared to a propagation direction of received unwanted sound waves. The speakers may transmit the inverted signal in a downward direction into the toilet bowl, in an upward direction out of the toilet bowl, or in a combination of directions based on a direction of the unwanted sound radiation. Additional microphones may be located on a toilet lid 724, on toilet tank 726, or at a remote location such as a bathroom door. The additional microphones may provide feedback about noise cancelation in order to calibrate the output of one or more speakers. Additional speakers may also be located on lid 724, on toilet tank 726, or at a remote location such as a bathroom door and may provide additional noise cancelation radiation. Microphones 706, 716, 714, 704, 718, and 720 may be located on or in a toilet seat as shown in FIG. 7. Microphones 706, 716, 714, 704, 718, and 720 may transmit in multiple directions including into the bowl and toward a user or a lid of the toilet. Lid 724, the toilet seat, or an inside of the toilet may be made of sound absorptive material such as mass loaded vinyl, high density material, anechoic material, or geometric sound canceling formations. Unwanted sound 708 is radiated from a bowl area of a toilet and received by microphone array 716. Microphone array 716 provides an unwanted sound wave signal to circuitry (not shown). The circuitry inverts the unwanted sound wave signal and outputs the inverted unwanted sound wave signal to one or more speakers 714. The speakers may be chosen based on a direction of propagation of the unwanted sound. The direction of propagation may be determined based on an array of microphones which may be located at microphone 716. The array may be formed in a hemispherical or spherical shape and the direction of propagation may be determined based on an intensity received at one or more microphones in the array. Speaker 714 may also comprise an array of speakers forming a hemispherical or spherical shape and one or more of the speakers 714 may be used to transmit the inverted unwanted sound wave signal 714 is a similar direction compared to the propagation direction of the unwanted sound wave 708. If microphone array 716 receives multiple unwanted sound waves which have different propagation directions, then multiple virtual signal point sources may be determined and multiple synthesized wave fronts may be sent by multiple speakers within an array of speakers in different propagation directions.

Figure 8:
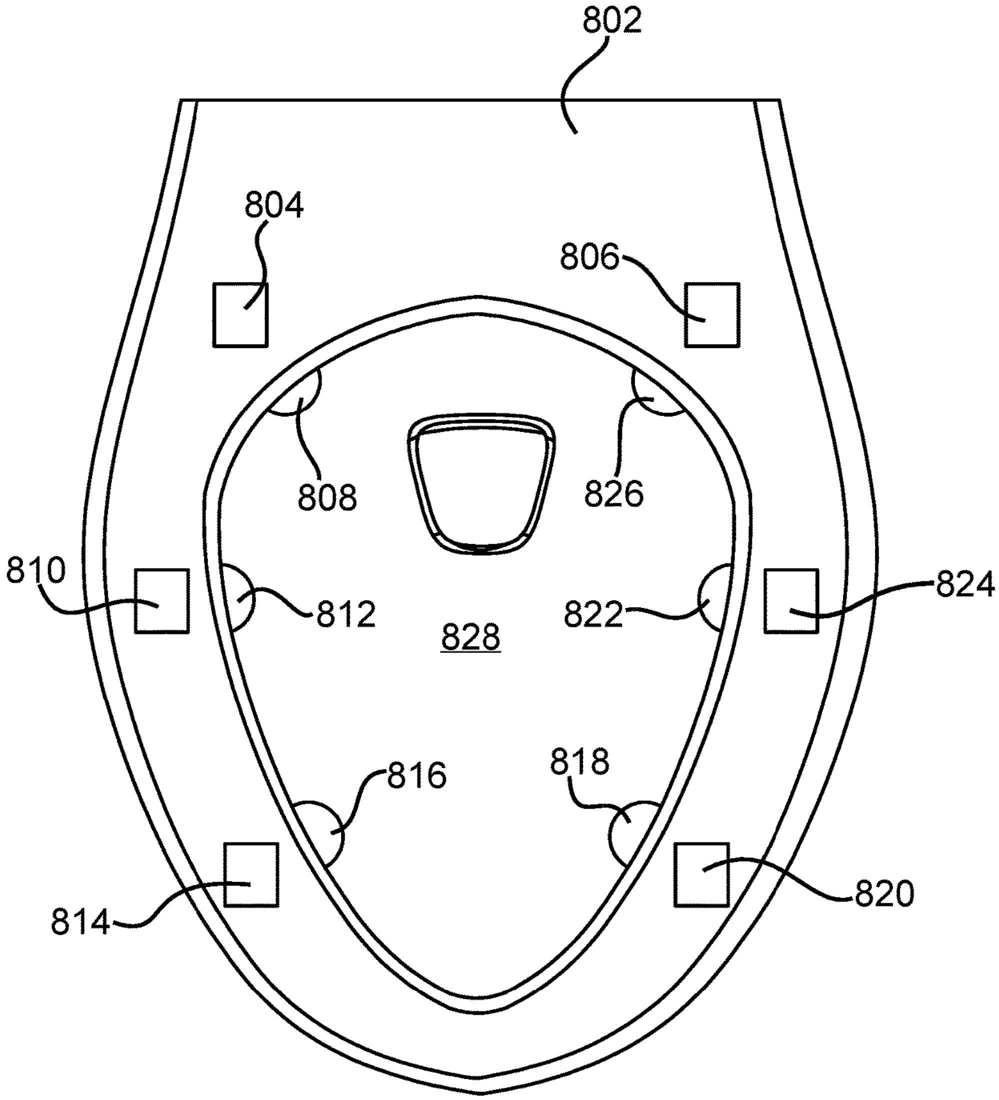
FIG. 8 is a top view of a toilet seat in accordance with an embodiment of the invention.

FIG. 8 shows a toilet seat 802 with speaker microphone combinations 804, 806, 808, 810, 812, 814, 816, 818, 820, 822, 824, and 826. Each speaker microphone combination 804, 806, 808, 810, 812, 814, 816, 818, 820, 822, 824, and 826 contains arrays of both speakers and microphones which may receive and transmit sound waves omni-directionally. The sound waves received and transmitted may be used for both noise cancelation and for audio communications. The noise cancelation may be for both free space noise cancelation and electronic noise cancelation. Free space noise cancelation may include reduction of urination noise, bowel movement noise, flatulence noise, toilet flushing noise, splashing water noise, or other noise generated within toilet bowl 828. Electronic noise cancellation may include audio communications which use the microphones and speakers on the toilet to cancel unwanted noise from a communication signal. Such communication signals may include telephone calls, intercom communications, and Internet transmissions. A toilet apparatus of the current invention may be used as a pairing device for hands free electronic communications without the worry of unwanted toilet noise being present in the electronic communication signal.

Figure 9:
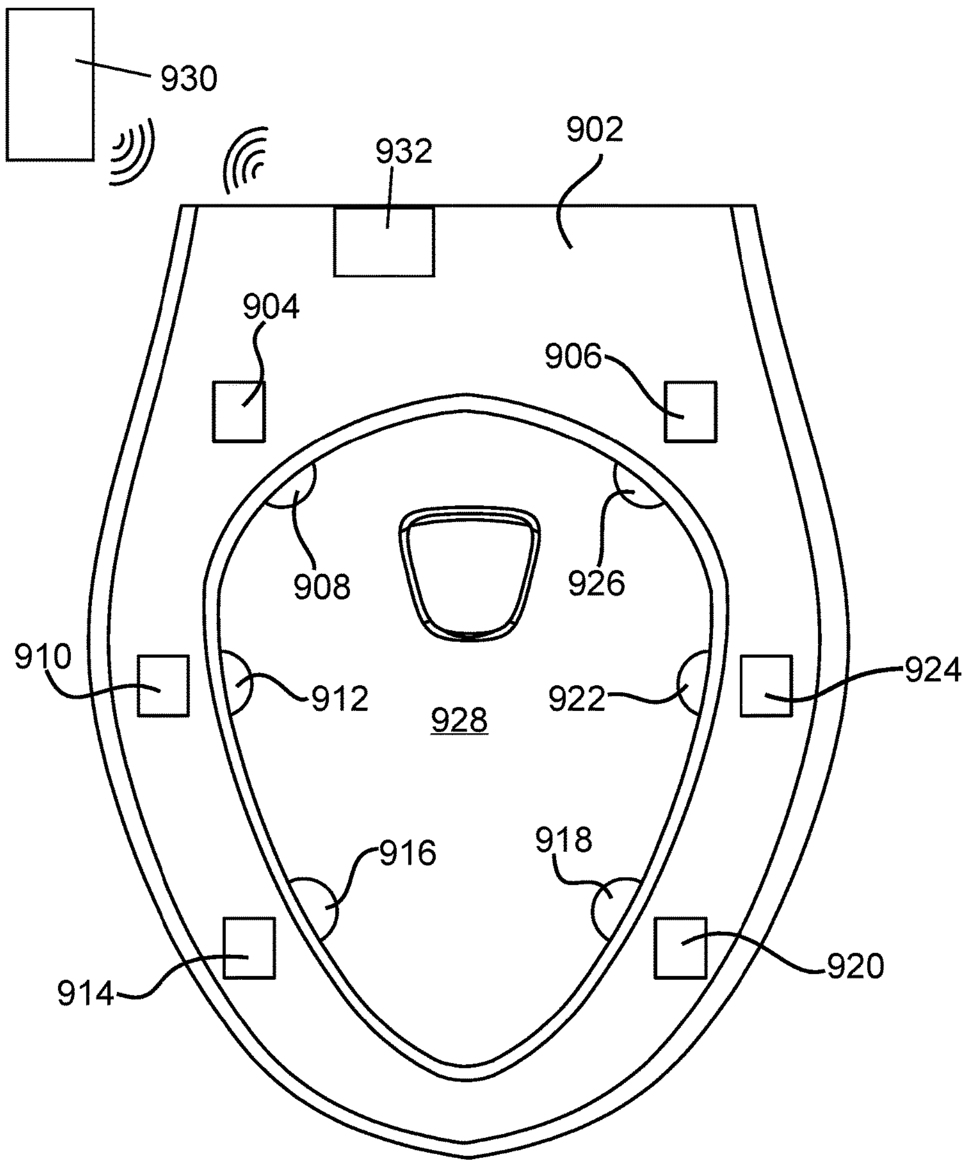
FIG. 9 is a top view of a toilet seat and a user device in accordance with an embodiment of the invention.

In FIG. 9, a user device 930 such as a telephone may be wirelessly connected to toilet seat 902. Toilets seat 902 may have a controller 932 including a processor, memory, a power source, and a wireless communications module. Each speaker microphone combination 904, 906, 908, 910, 912, 914, 916, 918, 920, 922, 924, and 926 contains arrays of both speakers and microphones which may receive and transmit sound waves omni-directionally. The sound waves received and transmitted may be used for both noise cancelation and for audio communications. The noise cancelation may be for both free space noise cancelation and electronic noise cancelation. Free space noise cancelation may include reduction of urination noise, bowel movement noise, flatulence noise, toilet flushing noise, splashing water noise, or other noise generated within a toilet bowl. Electronic noise cancellation may include audio communications which use the microphones and speakers on the toilet to cancel unwanted noise from a communication signal. Such communication signals may include telephone calls, intercom communications, and Internet transmissions. A toilet apparatus of the current invention may be used as a pairing device for hands free electronic communications without the worry of unwanted toilet noise being present in the electronic communication signal. For instance, a toilet user may desire to make a hands free phone call while using the toilet without the other party hearing any unwanted toilet noises. The toilet user may use a Bluetooth connection to connect with toilet controller 932. Toilet controller 932 may provide microphone and speaker functionality for user device 930 while electronically filtering and/or canceling unwanted toilet noises generated while using the toilet. Unwanted noises that may be filtered include shower noises, hair dryer noises, flushing, and noises radiating from within the toilet bowl 928.

Figure 10:
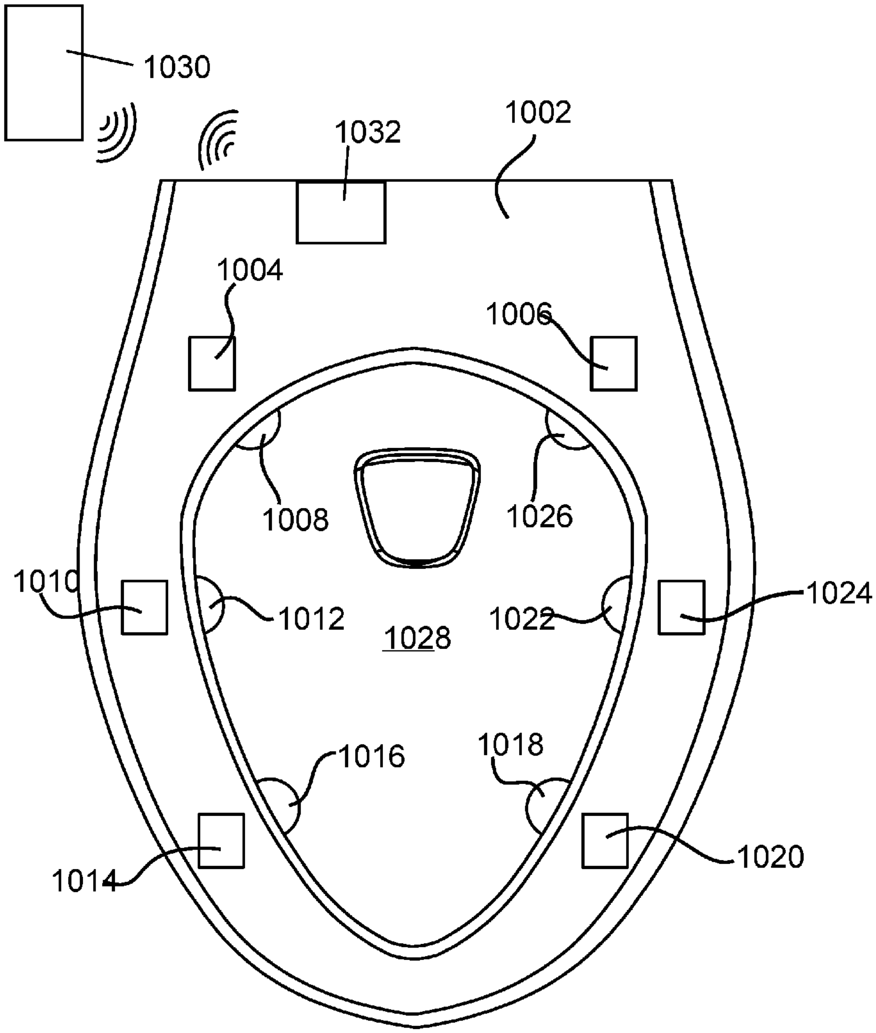
FIG. 10 is a top view of a toilet seat and a remote storage device in accordance with an embodiment of the invention.

In FIG. 10, a remote device 1030 such as a database server or computer may be wirelessly connected to toilet seat 1002 by way of a local or wide area network. Toilets seat 1002 may have a controller 1032 including a processor, memory, a power source, and a wireless communications module. Each speaker microphone combination 1004, 1006, 1008, 1010, 1012, 1014, 1016, 1018, 1020, 1022, 1024, and 1026 contains arrays of both speakers and microphones which may receive and transmit sound waves omni-directionally. The sound waves received and transmitted may be used for both noise cancelation and for toilet data collection. The noise cancelation may be for both free space noise cancelation and electronic toilet noise collection. Free space noise cancelation may include reduction of urination noise, bowel movement noise, flatulence noise, toilet flushing noise, splashing water noise, or other noise generated within a toilet bowl. Electronic noise collection may include audio data picked up by the microphones and speakers while a user is using the toilet. A communication device within controller 1032 may wirelessly transmit information gathered by the microphones to a remote computer or data collection system. The information transmitted may include noises from within the toilet including bowel movements, bowel movement frequency, urination duration, urination frequency, user speech, user commands, flatulence, etc. The information may be used to provide medical data to doctors, tracking of digestive health, tracking of urinary system health, or hydration information. Such communication signals may be transmitted and stored by way of Internet transmissions. Collected user data may be provided to a toilet user's doctor or may be kept for recording trends in the user's health related to noises obtained from microphones on the toilet. Speakers on the toilet may give users of the toilet feedback based on noises recorded. User feedback may include volume of urination feedback, frequency of urination within a given time frame, frequency of bowel movements within a given time frame, constipation information (based on bowel movement plopping noises and size of bowel movement information), etc. A user may be identified by voice recognition with in controller 1032 or my remote voice recognition by a network database server. A user account and profile may be kept and recorded based on toilet noises. User health trends may be reported based on stored data collected from toilet noises created by the user using a toilet.

The toilet and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A toilet apparatus comprising:

one or more arrays of microphones that detect unwanted sound waves associated with the toilet apparatus, wherein each of the one or more arrays of microphones comprises a plurality of microphones directed in a plurality of directions;

circuitry which determines one or more virtual point source locations of unwanted sound wave signals based on the detected unwanted sound waves;

a power supply that powers the circuitry; and one or more speakers that transmit one or more synthesized inverted unwanted wave fronts based on the one or more virtual point source locations; and a communication section, wherein the communication section transmits sounds gathered by the one or more arrays of microphones to a remote computer;

wherein at least one microphone within the plurality of microphones within at least one of the one or more arrays of microphones is configured to be used for voice recognition or for cancelation of the unwanted sound waves over a telephonic transmission.

2. A method of reducing toilet noise from a toilet comprising:

detecting one or more virtual point source locations of unwanted sound waves associated with the toilet with one or more arrays of microphones, wherein each of the one or more arrays of microphones comprises a plurality of microphones directed in a plurality of directions;

generating one or more synthesized inverted unwanted wave signals with one or more circuits based on the detected unwanted sound waves;

powering the one or more circuits with one or more power sources; and transmitting with one or more speakers one or more synthesized inverted unwanted wave fronts to a location within a toilet bowl and to a location outside of the toilet bowl; and transmitting sounds gathered by the one or more arrays of microphones to a remote computer;

wherein at least one microphone within the plurality of microphones within at least one of the one or more arrays of microphones is configured to be used for voice recognition or for cancelation of the unwanted sound waves over a telephonic transmission.

* * * * *